(12) United States Patent
Maile et al.

(10) Patent No.: US 6,238,813 B1
(45) Date of Patent: *May 29, 2001

(54) BATTERY SYSTEM FOR IMPLANTABLE MEDICAL DEVICE

(75) Inventors: Keith R. Maile, New Brighton; Jay A. Warren, North Oaks, both of MN (US)

(73) Assignee: Cardiac Pacemakers, Inc., St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/122,429

(22) Filed: Jul. 24, 1998

Related U.S. Application Data

(60) Provisional application No. 60/054,939, filed on Jul. 25, 1997.

(51) Int. Cl.[7] ....................................................... H01M 2/10
(52) U.S. Cl. ................................ 429/9; 429/99; 429/176; 607/36
(58) Field of Search ............................. 429/99, 9, 105, 429/163, 176; 607/36

(56) References Cited

U.S. PATENT DOCUMENTS

| | | | |
|---|---|---|---|
| 2,212,054 | 8/1940 | Spicer | 136/108 |
| 3,601,601 | 8/1971 | Eilenberger | 240/10.61 |
| 3,918,460 | 11/1975 | King et al. | 128/419 P |
| 3,926,198 | 12/1975 | Kolenik | 128/419 |
| 4,547,894 | 10/1985 | Benson et al. | 381/70 |
| 5,370,669 | 12/1994 | Daglow et al. | 607/36 |
| 5,405,363 | 4/1995 | Kroll et al. | 607/5 |
| 5,439,482 | 8/1995 | Adams et al. | 607/5 |
| 5,614,331 | 3/1997 | Takeuchi et al. | 429/9 |

FOREIGN PATENT DOCUMENTS

| | | |
|---|---|---|
| 3507092 | 8/1986 | (DE) . |
| 0771576 | 5/1997 | (EP) . |
| 0777286 | 6/1997 | (EP) . |

OTHER PUBLICATIONS

Abstract of Japanese Patent Publication No. 59–018576 (Kubo), published on Jan. 30, 1984, from Patent Abstracts of Japan, vol. 008, No. 103 (E–244), 1 pg., (May 1984).

*Primary Examiner*—John S. Maples
(74) *Attorney, Agent, or Firm*—Schwegan, Lundberg, Woessner & Kluth, P.A.

(57) ABSTRACT

A battery system and method of manufacture in which at least two batteries, having different chemistries, are integrated into a common housing. The battery system has a unitary housing having at least two chambers, in which each pair of adjacent chambers share a common wall. Each chamber contains one battery, and at least one battery has a different chemical composition than the remaining batteries.

40 Claims, 5 Drawing Sheets

BATTERY SYSTEM FOR IMPLANTABLE MEDICAL DEVICE

This application claims the benefit under 35 U.S.C. §109(e) of U.S. Provisional Application No. 60/054,939, filed on Jul. 25, 1997, which is hereby incorporated herein by reference.

TECHNICAL FIELD

The invention relates generally to electrochemical batteries and, in particular, to electrochemical batteries for use in implantable medical devices.

BACKGROUND

The battery of an implanted medical device should have a reliable, long life. Engineering progress in battery design has lead to substantial reductions in battery volume while maintaining, or improving upon, the device longevity. This reduction in battery volume has resulted in smaller and more comfortable devices for the patient.

Implantable cardiac defibrillators (ICDs) generally have monitoring and control circuitry to sense and analyze cardiac events, and electrical output circuitry to provide both pacing level and defibrillation level electrical energy to the cardiac tissue in response to the control circuitry. These ICD circuitry components, however, have different power requirements. While the monitoring and the pacing control and output circuitry require a continuous low-current supply over the life of the ICD, the defibrillation output circuitry require a high-current supply for very short time durations to enable the defibrillation electrical output circuitry to deliver a defibrillation level shock to the patient in a timely manner. Therefore, one of the challenges in designing ICDs is the integration of these circuitry components with vastly different power requirements into a ICD using a single current battery.

Typically, two lithium silver vanadium pentoxide batteries coupled in series have been used to achieve the high-current, high power density, requirements for the ICDs defibrillation output circuity. This high power capability battery design is suited for the high-voltage defibrillation output circuity which draws peak current drains on the order of amperes from the battery. By contrast, the low-current monitoring circuit, the logic control circuit, and any accompanying pacing output circuit of the ICD have peak battery demands in the microampere to milliampere range. The high power density batteries are typically regulated down to provide a stable low-current power supply to the monitoring and pacing control circuits over a wide range of potential battery loads. The down regulation of the power dense batteries is, however, an inefficient use of the depletable power source and thus a larger battery must be used to provide for the reliable operation of the ICD.

To resolve the dichotomy of combining high- and low-power circuits, the use of two separate batteries has been attempted. These "dual battery" systems provide two physically independent batteries matched to the separate power requirements of the ICD. U.S. Pat. Nos. 5,405,363 (Kroll et al.) and 5,439,482 (Adams et al.) describe the use of "dual battery" ICD systems. Each patent suggests that utilizing two batteries can result in a reduction of overall volume of the battery system as compared to a single battery system. While these patents describe reductions in ICD battery volumes, further reductions in battery volume and weight continue to be a goal of ICD designers.

SUMMARY OF THE INVENTION

The present battery system provides a dual battery system for use within an implantable medical device. The battery housings of the system share a common wall.

The shared common wall of the dual battery system reduces the weight and volume of the battery system, and thus the weight and volume of the implantable medical device. The result is a smaller, lighter, and more comfortable device for the patient.

The invention provides a battery system including (1) a unitary battery housing having a plurality of chambers; (2) a common wall between adjacent chambers; and (3) a plurality of batteries.

In one embodiment, the battery system has a unitary housing having at least two chambers, in which each pair of adjacent chambers share a common wall. Each chamber contains one battery, and at least one battery of the system has a different chemical composition than any or all of the remaining batteries.

In one application of the battery system, the battery is used in an ICD. The battery system comprises a unitary housing having a plurality of walls defining a first and a second chamber. The plurality of walls includes a common wall between the first chamber and the second chamber. Housed within the first chamber is a first electrochemical cell having a first cathode, a first anode, and a first electrolyte between the first cathode and the first anode. The second chamber houses a second cathode, a second anode, and a second electrolyte between the second cathode and the second anode. The two electrochemical cells have different chemical compositions such that one electrochemical cell can supply, for example, a energy dense low current output, in the microampere range, while the other electrochemical cell can supply a power dense high current output, in the ampere range. In this way the battery system can supply the distinct electrical needs of the various components of the implanted device while conserving both volume and weight of the implanted device.

In alternative embodiments, different numbers and locations of chambers can also be used to house the electrochemical cells. When only first and second chambers are used, they share an entire housing wall. However, when three or more chambers are used it is possible to have each chamber sharing a housing wall with more than one of the remaining chambers. In this way, further reductions in both volume and weight of the implanted device can be attained.

DETAILED DESCRIPTION

In the following Detailed Description, reference is made to the accompanying drawings which form a part hereof and in which is shown by way of illustration specific embodiments in which the invention may be practiced. These embodiments are described in sufficient detail to enable those skilled in the art to practice and use the invention, and it is to be understood that other embodiments may be utilized and that electrical, logical, and structural changes may be made without departing from the spirit and scope of the present invention. The following detailed description is, therefore, not to be taken in a limiting sense and the scope of the present invention is defined by the appended claims and their equivalents.

Figure 1:
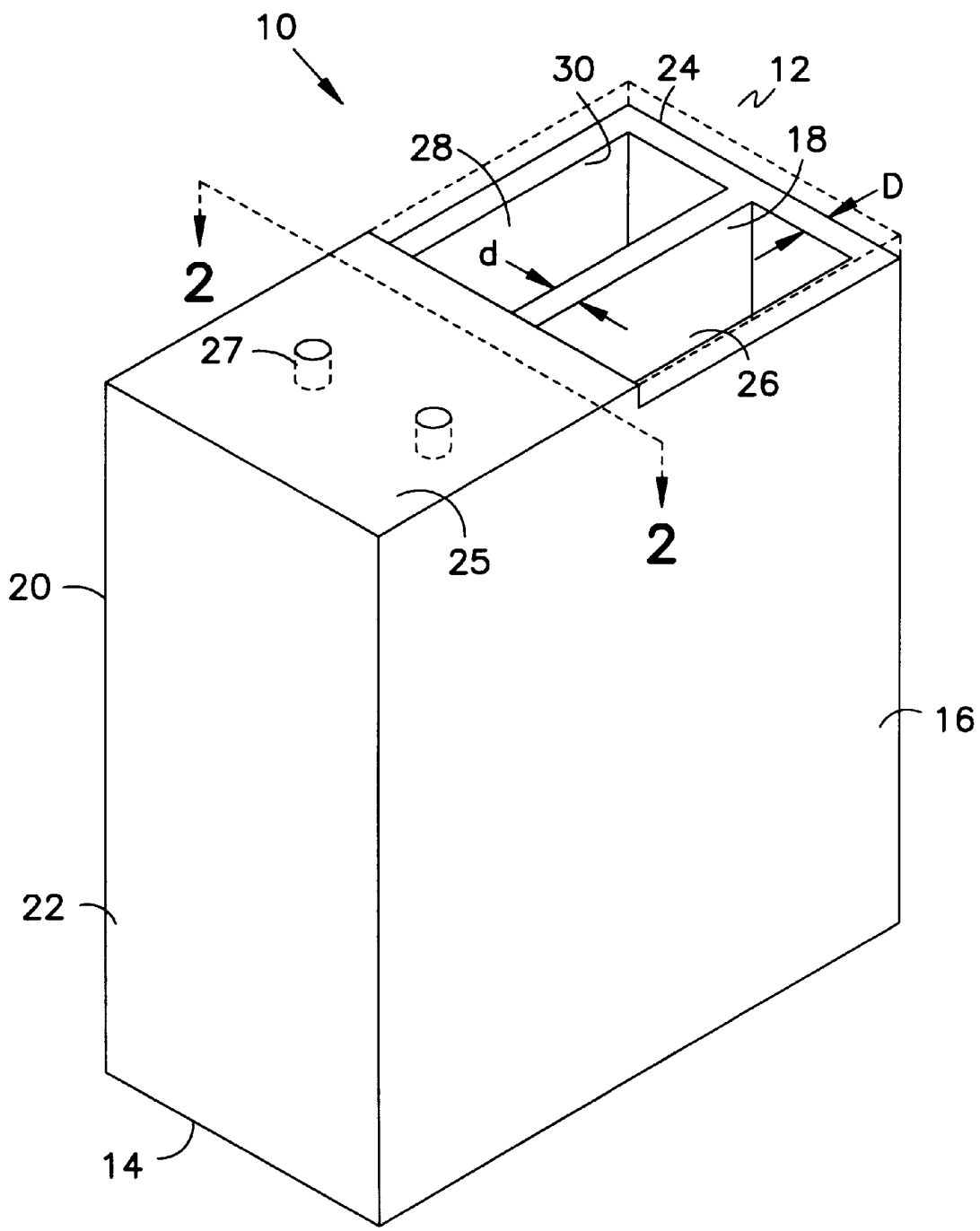
FIG. 1 is a schematic view of one embodiment of the battery system from which a segment of the lid of the housing has been removed to show detail.
Figure 2:
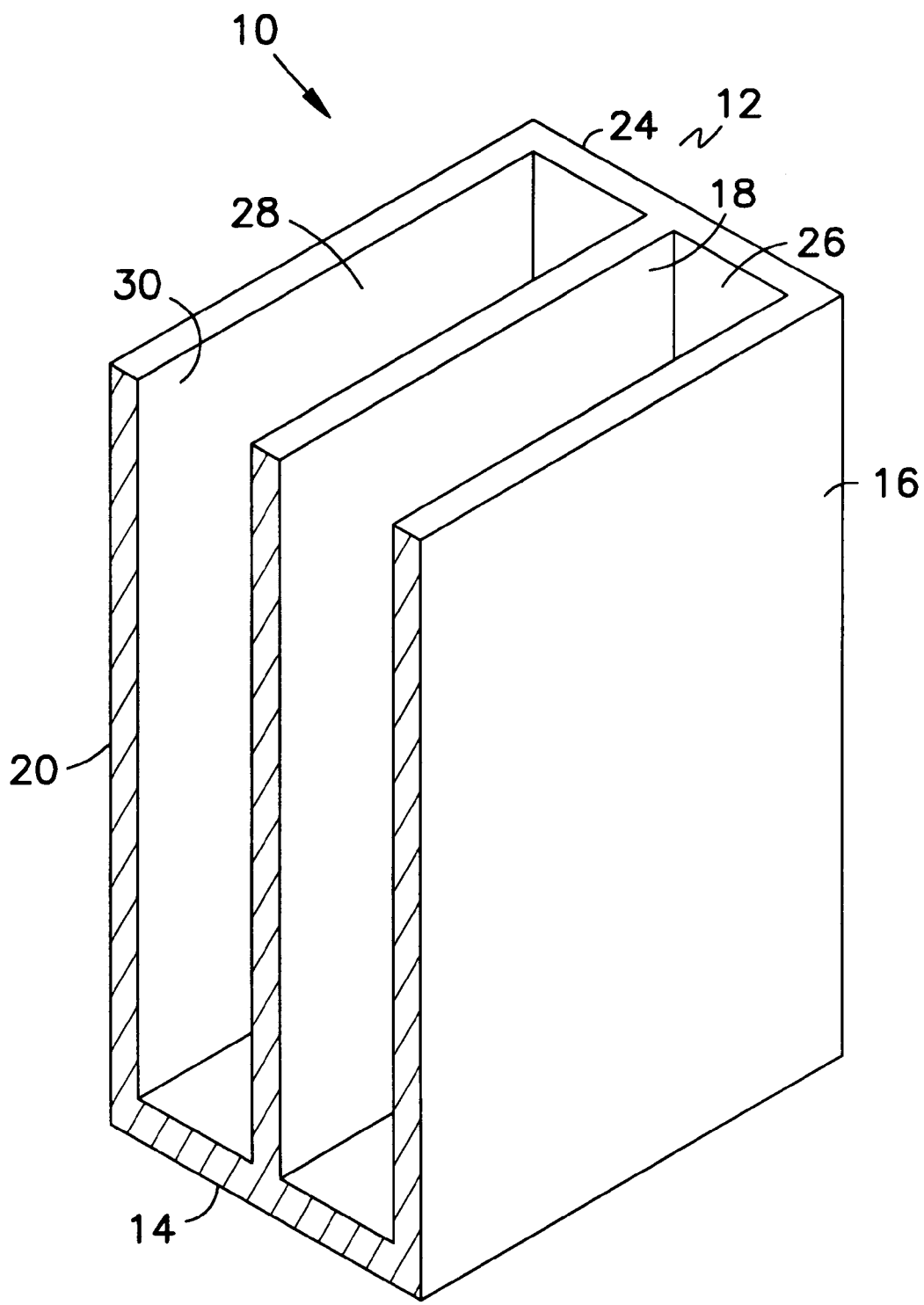
FIG. 2 is a schematic view of a FIG. 1 taken along the lines 2—2 of FIG. 1.

FIGS. 1 and 2 of the drawing show a first embodiment of a battery system 10. The battery system 10 is adapted to be used within an implantable medical device for supplying electrical energy to the various components of the implantable medical device.

The battery system 10 comprises a unitary housing 12 of metal such as stainless steel or titanium which is shaped or otherwise formed to have a first plurality of walls which define a second plurality of battery chambers, the second plurality of chambers defining a volume for one or more battery cells. The battery chambers can be rectangular in shape or they can be defined by a volume having a parabolic or a cylindrical segment cross section. The battery chambers are also of an integral construction where the second plurality of battery chambers share one or more common walls, and the housing geometrically defined to reside within the implantable medical device.

Each chamber includes a bottom portion 14; spaced-apart side wall portions 16, 18, and 20 extending from the bottom portion; and spaced-apart end wall portions 22 and 24 and the latter portions extend from bottom portion 14 to join the side wall portions 16, 18, and 20, and thus form the second plurality of hollow battery chambers. The bottom portion 14 is planar, and the side wall portions 16, 18, and 20 are parallel, but this is not mandatory. The unitary housing has a top or end, opposite the bottom portion 14, which is sealed closed by means of a lid 25 also of metal such as stainless steel or titanium.

The plurality of battery chambers also include at least one common wall between adjacent pairs of chambers. Therefore, the housing provides an electrically common contact for two or more of the second plurality of battery chambers. In FIGS. 1 and 2 the side wall portion 18 provides an example of a common wall that lies between adjacent pairs of battery chambers. While this example shows the common wall comprising one entire side of the adjacent pairs of battery chambers, is possible that the common wall can be a portion of the adjacent walls such that the battery chambers are in a staggered configuration. Alternatively, each battery chamber can share a common wall with two or more adjacent battery chambers when the battery system has three or more battery chambers present.

The side wall portions 16, 18, 20, the end wall portions 22, 24, the bottom portion 14, and the lid 25 each have a thickness. The side wall portion 18 has a thickness "d" and the remaining side walls 16 and 20, end walls 22 and 24, bottom portion 14, and the lid 25 have a thickness "D". In one embodiment of the present invention, any wall of the unitary housing 12 has a thickness of less than 0.5 millimeters. In another embodiment, a range of thickness for any wall of the unitary housing 12 is between 0.2–0.5 millimeters. The thickness d, in one embodiment, can have a value that is equal to D. However, in an alternative embodiment, d is less than D wherein the thickness d is in the range of 0.2–0.4 millimeters and the thickness of D is in the range of 0.3–0.5 millimeters.

Each of the second plurality of battery chambers is adapted to house one or more battery cells, where battery cells are electrochemical cells, within a separate chamber where at least one of the electrochemical cells has a different chemical composition than any other electrochemical cell.

Briefly, the method of manufacturing the battery system of the present invention comprises the steps of constructing a housing providing a plurality of chambers, where the plurality of chambers define a volume for one or more battery cells and where the plurality of chambers share one or more common walls. The housing is further constructed such that it is geometrically defined to reside within the implantable device. An anode is placed into each of the plurality of battery chambers. The anode comprises a pair of alkali metal elements or plates having an anode current collector sandwiched or positioned between the anode elements. In one embodiment, the anodes of the battery system are a lithium compound. A conductor strip of nickel or suitable metal is spot welded to the anode current collector. An electrical conductor is connected to the conductor strip. The electrical conductor extends out of the unitary housing and through an opening in the lid 25 to provide an external electrical connection point ("terminal"). The anodes are coated with an organic electron donor component material by placing an electrolyte compound into physical contact with each exposed surface of the anodes.

The electrolyte is comprised of an organic solvent (including acetonitrile, γ-butyrolactone, dimethylsulfoxide, dimethylsulfite, 1,2-dimethoxyethane, dioxolane, methyl formate, nitromethane, or prorylene carbonate) and lithium salts. The electrical conductor is then sealed from the remainder of the cell.

The electrochemical cells further include a cathode element within each of the plurality of battery chambers. The cathode element is in operational contact with exposed surfaces of the coated anode surfaces and also in operational contact with the inner surface 30 of the unitary housing. The unitary housing is constructed of an electrically conducting material, and it serves as a cathode current collector. The cathode current collector is then coupled to a cathode terminal which extends to the exterior of the battery housing. The cathode terminal is then connected to an opening 27 through the lid 25 (or is a part of the lid 25) of the battery system and of the cathode current collector. The lid 25 of the battery system is then fitted into place over the open end of the unitary housing and is welded around the peripheral edge of the unitary housing to create a hermetic seal. Each electrochemical cell is activated by placing the cathode material into physical contact with the electrolyte compound to create the plurality of cells or batteries.

Each battery chamber houses a separate electrochemical cell, and at least one of the plurality of electrochemical cells has a different chemical composition than any other electrochemical cell. In this way, at least one of the electrochemical cells of the battery system has a different power density as compared to the power density of any other electrochemical cell within the battery system. The electrochemical cells of the battery system can be, but are not limited to, manufactured from materials which comprise an anode of an alkali metal such as lithium, a cathode selected from the group consisting essentially of iodide, vanadium oxide (including vanadium pentoxide), silver vanadium oxide, silver chromium oxide, cobalt oxide, manganese oxide, and carbon monofloride, and an electrolyte which is a liquid organic compound.

In an alternative embodiment, the second plurality of battery chambers can be electrically isolated from each other through the use of an electrically insulating material which is used to electrically separate the plurality of battery chambers. Any relatively non-conductive material may be used to perform electrical insulation.

In one embodiment of the invention, the second plurality of chambers includes a first battery chamber 26 and a second battery chamber 28. The first battery chamber 26 has a first geometrical shape and the second battery chamber 28 has a second geometrical shape, where the first geometrical shape substantially equal to the second geometrical shape. Alternatively, the first geometrical shape could be substantially different to the second geometrical shape. The first and second battery chambers 26 and 28 are rectangular parallelepiped in shape. They form an integral construction including a bottom portion 14; spaced-apart side wall portions 16, 1 8, and 20 extending from the bottom portion; and spaced-apart end wall portions 22 and 24 and thus the latter portions extend from bottom portion 14 to join the side wall portions 16, 18, and 20 to form the first and second battery chambers 26 and 28. The plurality of walls forming the first and second battery chambers 26 and 28 include the side wall portion 18 which constitutes the common wall between the first chamber 26 and the second chamber 28.

A first electrochemical cell is housed within the first battery chamber 26. In the present embodiment the first electrochemical cell has a first anode of lithium, a first cathode selected from the group consisting essentially of iodide, silver vanadium pentoxide, and vanadium pentoxide, and a first liquid organic electrolyte compound. The second electrochemical cell is comprised of an anode, cathode, and an electrolyte that together provide a different chemical composition than the first electrochemical cell. Thus, the battery system has first and second electrochemical cells which provide different energy densities and power densities. In the present embodiment the second electrochemical cell has an anode of lithium, a cathode of carbon monofloride, and a liquid organic electrolyte compound.

Figure 3:
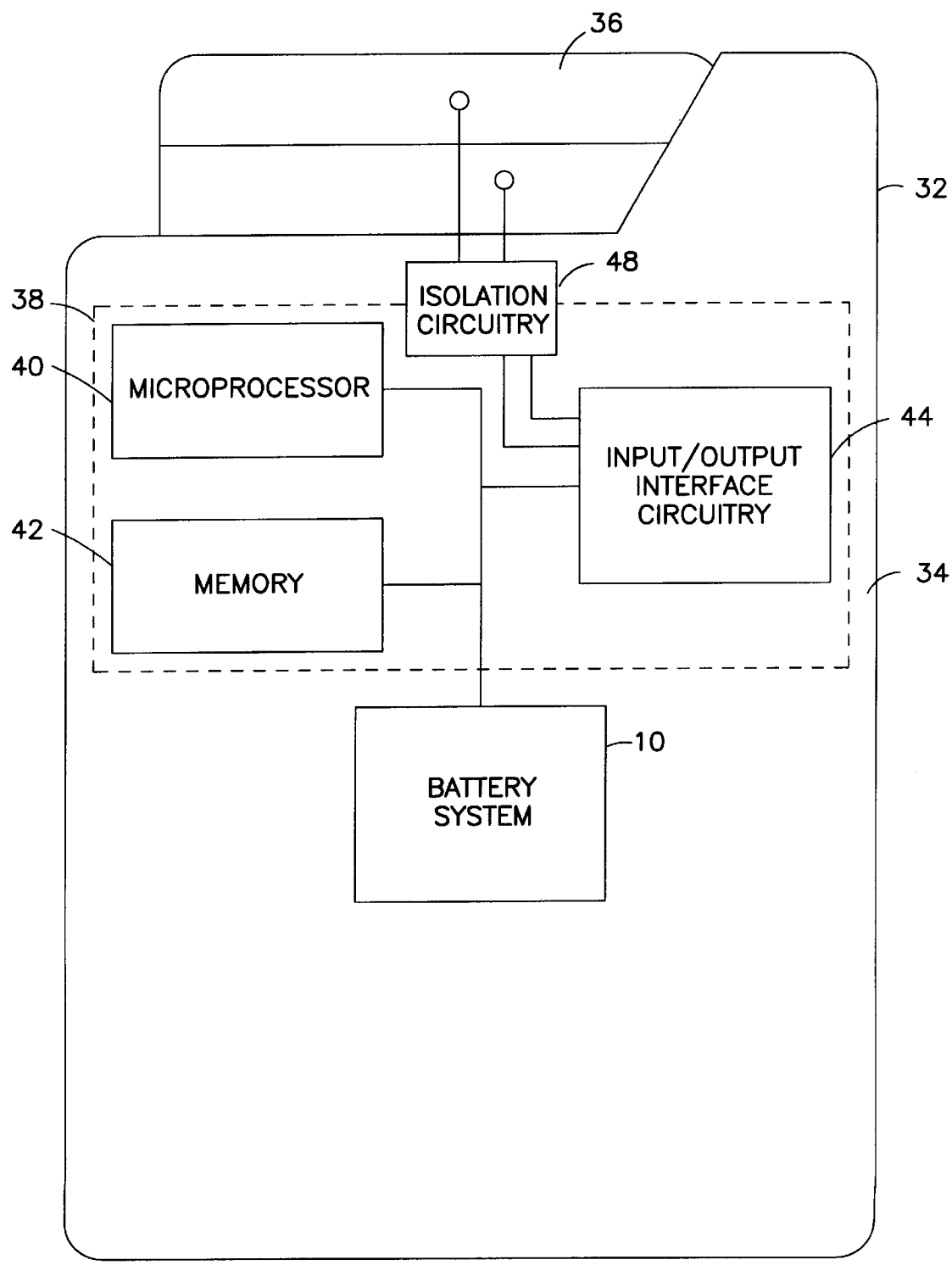
FIG. 3 is a schematic view of one embodiment of a block diagram of electronic control circuitry utilizing the battery system according to the present invention.

Referring now to FIG. 3, there is shown the battery system of the invention housed within an ICD 32 where it supplies the distinct electrical needs of the various components of the ICD, while conserving both volume and weight of the ICD. The general ICD system has an implantable housing 34 on which is mounted a connector block 36. The connector block 36 has a plurality of connector ports for physically and electrically connecting various implantable transvenous catheters, and other implantable electrodes, to the ICD 32.

Within the ICD 32, the implantable catheters are electrically connected to integrated circuitry controls 3 8, which incorporate a microprocessor 40, having sensing and logic control circuits, a memory section 42, including RAM and ROM, and an input/output interface circuitry 44, containing sense amplifiers and pacing and defibrillation pulse generator circuitry. The sensing control circuits of the microprocessor 40 receive electrically sensed cardiac signals from a ventricle and/or an atrium, and employ sense amplifiers contained within the input/output interface circuitry 44. The logic control circuits of the microprocessor 40 then analyze the sensed cardiac signals using rhythm detection and discrimination algorithms, contained within the memory 42 sections of the ICD 32, to identify signals indicating the onset of an arrhythmia of the heart.

The input/output interface circuitry 44 can then deliver pacing pulses and defibrillation shocks to restore normal sinus rhythm to the heart. The pacing and defibrillation pulse generator circuitry both incorporate capacitors which are used to supply electrical energy to the heart. The pacing pulse generator circuitry requires the ICD battery system 10 to charge the pacing capacitor to a point that it can deliver a continuous series of pacing pulses in the 1 to 10 volt range. However, the defibrillation pulse generator circuitry also requires the ICD battery 46 to charge the high-voltage defibrillation capacitor to a point where it can deliver a defibrillation sized shock of up to 750 volts, and generate it quickly enough to be of clinical utility. The memory 42 section of the ICD 32 further includes a diagnostic data storage component to assist a physician in reconstructing a clinical event. Also incorporated into the ICD 32 are isolation and protection circuitry 48.

By providing two distinct power sources, the battery system 10 can provide the optimal power supply for the high power density (high-current) defibrillation circuitry and the high energy density (low-current) sensing/pacing circuitry of the ICD system, while the unitary housing of the invention concurrently minimizes the size and the weight of the battery system. In one embodiment, the battery system 10 has a displacement volume below 40 cubic centimeters. Other embodiments exist with various displacement volume ranges and the examples are not intended in an exclusive or limiting sense.

The first cell of the battery system 10 should have a total energy storage capacity of at least 3 watt-hours to provide adequate voltages to the sensing and pacing circuits of the ICD over at least a two year period. Furthermore, the first electrochemical cell is a high energy density, low-voltage battery, such as a lithium iodine cell, having a first power output between 1–250 microwatts. The first electrochemical cell can be incorporated into the first battery chamber 26 of the battery system 10 to supply power to the sensing and logic control circuits of the microprocessor 40 of FIG. 3. The first electrochemical cell can also supply power to the pacing output circuitry, which can have a peak power demands from the battery system on the order of 100 to 200 microwatts.

In contrast, the second cell should have an energy storage capacity of at least 3 watt-hours to provide adequate voltages for the defibrillation output circuitry of the ICD for at least a two year period. The second electrochemical cell can be a high power density low-internal-impedance chemistry battery, such as a lithium-silver vanadium oxide cell, having a second output between 0.5–30 watts. The second electrochemical cell is incorporated into the second battery chamber 28 of the battery system 10 to supply power to the high-voltage defibrillation circuits, which develop and deliver outputs up to 750 volts (approximately 15–40 Joules), and can impose peak current drain demands of several amperes on the power source.

Figure 4:
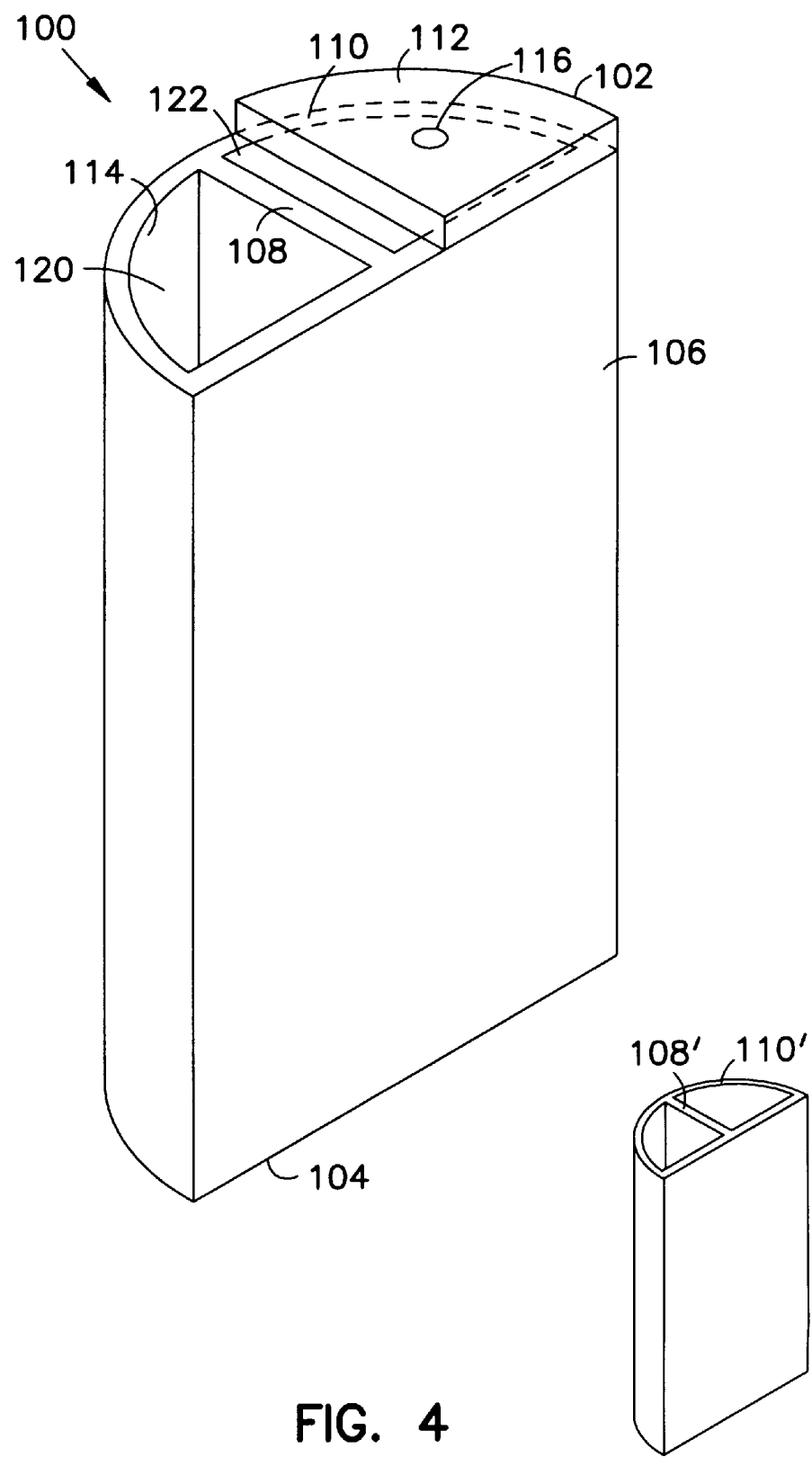
FIG. 4 is a schematic view of one embodiment of the battery system from which a segment of the lid of the housing has been removed to show detail.

FIG. 4 of the drawings shows another embodiment of the battery system of the present invention. The battery system 100 of FIG. 4 is adapted to be used within an implantable medical device for supplying electrical energy to the various components of the implantable medical device as previously described.

The battery system 100 comprises a unitary housing 102 of metal such as stainless steel or titanium which is shaped or otherwise formed to have a first plurality of walls which define a first and second battery chamber 120 and 122.

The first and second battery chambers 120 and 122 are semi-cylindrical and shaped as a quarter of a cylinder. They form an integral construction including a bottom portion 104; spaced-apart wall portions 106, 108, and 110 extending from the bottom portion 104 to form the first and second battery chambers 120 and 122. The bottom portion 104, the wall portions 106 and 108 are planar, and the wall portion 110 is arcuvet, so that the walls define a quarter of a cylinder divided along its axis and wherein the housing defines a tubular shape or, alternatively, a partial spheroid shape. Alternatively, the wall portion 110' can be constructed to be a partial ellipsoid, wherein the wall portion 108' extends along the long axis of the ellipsoid and the housing defines a parabolic segment. The unitary housing has a top or end, opposite the bottom portion 104, which is sealed closed by means of a lid 112 also of metal such as stainless steel or titanium.

The plurality of battery chambers of the invention also includes at least one common wall between adjacent pairs of chambers. In FIG. 4 the wall portion 108 provides an example of a common wall that lies between adjacent pairs of battery chambers. The wall portions 106, 108, 110, the bottom portion 104 and the lid 112 each have a thickness. The wall portion 108 has a thickness "d" and the remaining walls 106 and 110, bottom portion 104, and lid 112 have a thickness "D". In one embodiment of the present invention, any wall of the unitary housing 102 has a thickness of less than 0.5 millimeters. In another embodiment, a range of thickness for any wall of the unitary housing 102 is between 0.2–0.5 millimeters. The thickness d, in one embodiment, can have a value that is equal to D. However, in an alternative embodiment, d is less that D wherein the thickness d is in the range of 0.2–0.4 millimeters and the thickness of D is in the range of 0.3–0.5 millimeters.

Each of the plurality of battery chambers is adapted to house an electrochemical cell or battery. As previously described, the battery chemistry used within the separate battery chambers can be selected to provide a first power of between 1–250 microwatts in one battery chamber and a second power of between 0.5–30 watts in the second battery chamber.

Figure 5:
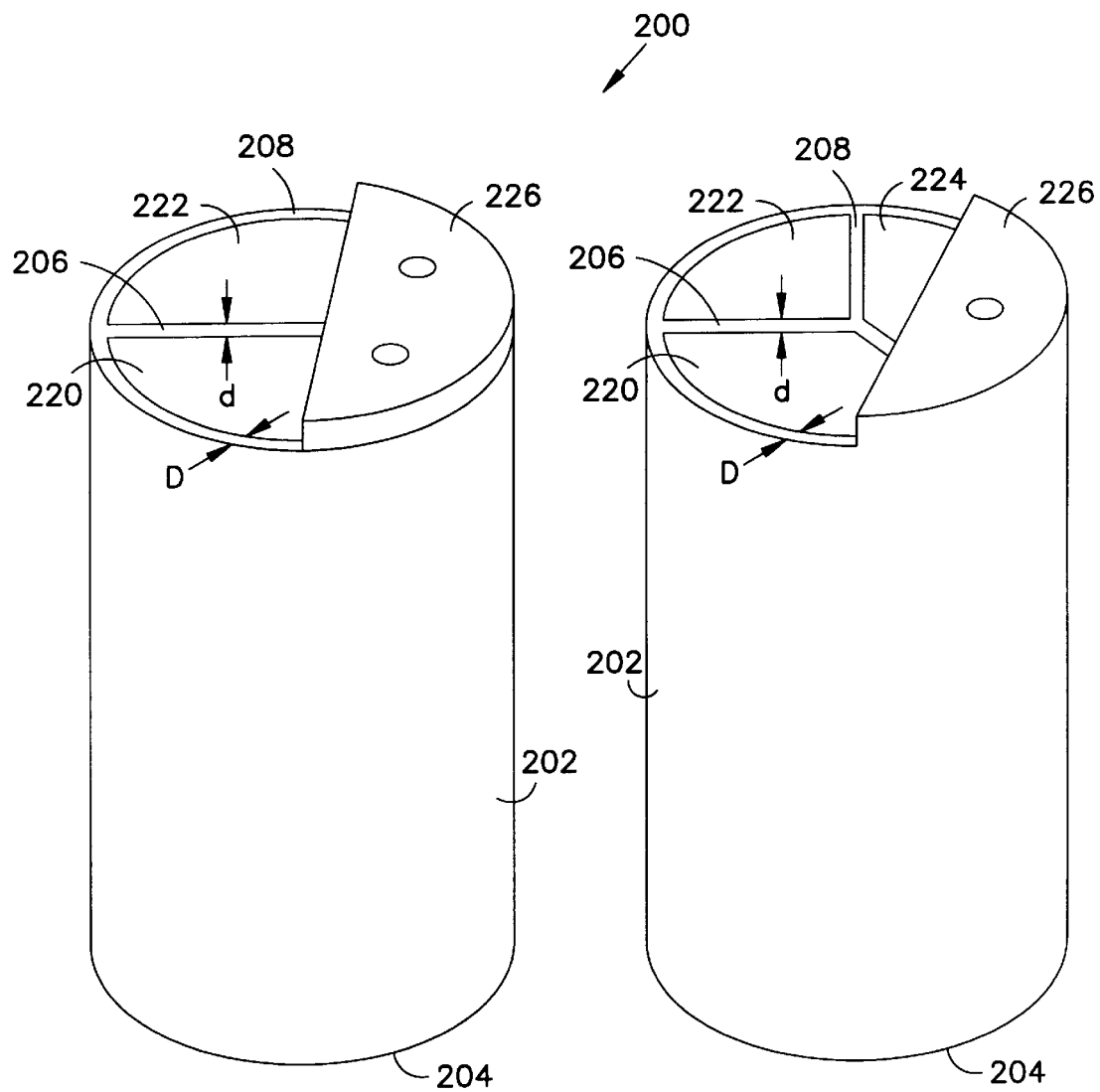
FIG. 5 is a schematic view of one embodiment of the battery system from which a segment of the lid of the housing has been removed to show detail.

FIG. 5 of the drawings show another embodiment of a battery system of the present invention. The battery system 200 of FIG. 5 is adapted to be used within an implantable medical device for supplying electrical energy to the various components of the implantable medical device.

The battery system 200 comprises a unitary housing 202 of metal such as stainless steel or titanium which is shaped or otherwise formed to have a first plurality of walls which define a first and second battery chamber 220 and 222. The first and second battery chambers 220 and 222 are arcuvet in shape. The battery chambers form an integral construction including a bottom portion 204; spaced-apart wall portions 206 and 208 extending from the bottom portion 204 to form the first and second battery chambers 220 and 222. The battery system 2000 can also include a third battery chamber 224. The bottom portion 204 and the wall portion 206 are planar, and the wall portion 208 is tubular. The unitary housing has a top or end, opposite the bottom portion 204, which is sealed closed by means of a lid 226 also of metal such as stainless steel or titanium.

The plurality of battery chambers of the invention also includes at least one common wall between adjacent pairs of chambers. In FIG. 5 the wall portion 206 provides an example of a common walls that lies between adjacent pairs of battery chambers. The wall portions 206, 208, the bottom portion 204 and the lid 226 each have a thickness. The wall portion 206 has a thickness "d" and the wall portion 208, bottom portion 204, and lid 226 have a thickness "D". In one embodiment of the present invention, any wall of the unitary housing 202 has a thickness of less than 0.5 millimeters. In another embodiment, a range of thickness for any wall of the unitary housing 202 is between 0.2–0.5 millimeters. The thickness d, in one embodiment, can have a value that is equal to D. However, in an alternative embodiment, d is less that D wherein the thickness d is in the range of 0.2–0.4 millimeters and the thickness of D is in the range of 0.3–0.5 millimeters.

Each of the plurality of battery chambers is adapted to house an electrochemical cell or battery. As previously described, the battery chemistry used within the separate battery chambers can be selected to provide a first power of between 1–250 microwatts in one battery chamber and a second power of between 0.5–30 watts in the second battery chamber.

We claim:

1. A battery system, comprising:
    a housing having a plurality of walls defining a plurality of chambers, where the plurality of chambers share one or more common walls and two or more of the plurality of chambers provide a volume for one or more battery cells and where the housing provides an electrically common contact for at least two of the plurality of chambers; and
    the housing geometrically defined to reside within an implantable medical device.

2. The battery system of claim 1, including an implantable medical device, the implantable medical device comprising an implantable housing, and the battery system within the implantable housing for supplying electrical energy to the implantable medical device.

3. The battery system of claim 1, wherein the one or more battery cells are electrochemical cells.

4. The battery system of claim 3, wherein the electrochemical cells include an anode of lithium, a cathode selected from the group consisting of iodide, vanadium oxide, vanadium pentoxide, silver vanadium oxide, silver chromium oxide, cobalt oxide, manganese oxide, and carbon monofloride, and an electrolyte which is an organic solvent and lithium salts.

5. The battery system of claim 3, wherein each of the electrochemical cells has a total energy storage capacity of at least 3 watt-hours.

6. The battery system of claim 3, wherein the electrochemical cells include a first cell and a second cell, and where a chemical composition of the first cell is different than a chemical composition of the second cell.

7. The battery system of claim 6, wherein the first cell has a first power output between 1–250 microwatts, and the second cell has a second power output of between 0.5–30 watts.

8. The battery system of claim 1, wherein the plurality of chambers includes a first chamber and a second chamber, and where the first chamber has a first geometrical shape and the second chamber has a second geometrical shape, the first geometrical shape substantially equal to the second geometrical shape.

9. The battery system of claim 1, wherein the plurality of chambers includes a first chamber and a second chamber, and where the first chamber has a first geometrical shape and the second chamber has a second geometrical shape, the first geometrical shape substantially different than the second geometrical shape.

10. The battery system of claim 1, wherein the housing defines a rectangular parallelepiped shape.

11. The battery system of claim 1, wherein the housing defines a tubular shape.

12. The battery system of claim 1, wherein the housing defines a partial spheroid shape.

13. The battery system of claim 1, wherein the battery system has a displacement volume of below 40 cubic centimeters.

14. The battery system of claim 1, wherein any wall of the housing is less than 0.5 millimeters thick.

15. The battery system of claim 1, wherein any wall of the housing is between 0.2–0.5 millimeters thick.

16. The battery system of claim 1, wherein the housing is made of surgical grade stainless steel.

17. The battery system of claim 1, wherein the housing is made of titanium or alloys of titaniumn.

18. The battery system of claim 1, wherein the housing is hermetically sealed.

19. An implantable medical device, comprising:

an implantable housing; and a battery system within the implantable housing for supplying electrical energy to the implantable medical device, in which the battery system comprises a housing having a first plurality of walls defining a plurality of chambers, two or more of the chambers definng a volume for one or more battery cells, the plurality of chambers sharing one or more common walls, and where the housing provides an electrically common contact for at least two of the plurality of chambers; and the housing geometrically defined to reside within the implantable medical device.

20. The implantable medical device of claim 19, wherein the one or more battery cells are electrochemical cells.

21. The implantable medical device of claim 20, wherein the electrochemical cells include an anode of lithium, a cathode selected from the group consisting of iodide, vanadium oxide, vanadium pentoxide, silver vanadium oxide, silver chromium oxide, cobalt oxide, manganese oxide, and carbon monofloride, and an electrolyte which is an organic solvent and lithium salts.

22. The implantable medical device of claim 20, wherein each of the electrochemical cells has a total energy storage capacity of at least 3 watt-hours.

23. The implantable medical device of claim 20, wherein the electrochemical cells include a first cell and a second cell, and where a chemical composition of the first cell is different than a chemical composition of the second cell.

24. The implantable medical device of claim 1, wherein the first cell has a first power output between 1–250 microwatts, and the second cell has a second power output of between 0.5–30 watts.

25. The implantable medical device of claim 19, wherein the plurality of chambers includes a first chamber and a second chamber, and where the first chamber has a first geometrical shape and the second chamber has a second geometrical shape, the first geometrical shape substantially equal to the second geometrical shape.

26. The implantable medical device of claim 19, wherein the plurality of chambers includes a first chamber and a second chamber, and where the first chamber has a first geometrical shape and the second chamber has a second geometrical shape, the first geometrical shape substantially different than the second geometrical shape.

27. The implantable medical device of claim 19, wherein the housing defines a rectangular parallelepiped shape.

28. The implantable medical device of claim 19, wherein the housing defines a tubular shape.

29. The implantable medical device of claim 19, wherein the housing defines a partial spheroid shape.

30. The implantable medical device of claim 19, wherein the battery system has a displacement volume of below 40 cubic centimeters.

31. The implantable medical device of claim 19, wherein any wall of the housing is less than 0.5 millimeters thick.

32. The implantable medical device of claim 19, wherein any wall of the housing is between 0.2–0.5 millimeters thick.

33. The implantable medical device of claim 19, wherein the housing is made of surgical grade stainless steel.

34. The implantable medical device of claim 19, wherein the housing is made of titanium or alloys of titanium.

35. The implantable medical device of claim 19, wherein the housing is hermetically sealed.

36. A method for manufacturing a battery system, comprising:

constructing a housing providing a plurality of chambers, two or more chambers of the plurality of chambers providing a volume for one or more battery cells, the two or more chambers sharing one or more common walls, where the housing provides an electrically common contact for at least two of the plurality of chambers, and where the housing is geometrically defined to reside within an implantable device.

37. The method for manufacturing the battery system of claim 36, wherein the plurality of chambers includes a first chamber and a second chamber, and the one or more battery cells includes a first electrochemical cell and a second electrochemical cell, and encasing the first electrochemical cell in the first chamber and encasing the second electrochemical cell in the second chamber.

38. The method for manufacturing the battery system of claim 36, including utilizing the one or more battery cells with an implantable medical device for supplying electrical energy to the implantable medical device.

39. The method for manufacturing the battery system of claim 36, including constructing the one or more battery cells from an anode of lithium, a cathode selected from the group consisting of iodide, vanadium oxide, vanadium pentoxide, silver vanadium oxide, silver chromium oxide, cobalt oxide, manganese oxide, and carbon monofloride, and an electrolyte which is an organic solvent and lithium salts.

40. The method for manufacturing the battery system of claim 36, including constructing a first electrochemical cell and a second electrochemical cell for the one or more battery cells, where a chemical composition of the first electrochemical cell is different than a chemical composition of the second electrochemical cell.

\* \* \* \* \*

UNITED STATES PATENT AND TRADEMARK OFFICE
CERTIFICATE OF CORRECTION

PATENT NO. : 6,238,813 B1
DATED : May 29, 2001
INVENTOR(S) : Keith R. Maile and Jay A. Warren It is certified that error appears in the above-identified patent and that said Letters Patent is hereby corrected as shown below:

Title page,
Item [75], delete "Keith R. Maile, New Brighton;" and insert -- Keith R. Maile, Lino Lakes --, therefor.

Column 2,
Line 1, Combine ¶ beginning with "The shared common wall .." with ¶ ending with "… a common wall.".

Column 4,
Line 25, Combine ¶ beginning with "The electrolyte is comprised …" with ¶ ending with "… of the anodes.".

Column 5,
Line 48, delete "3 8" and insert -- 38 --, therefor.

Column 9,
Line 17, delete "definng" and insert -- defining --, therefor.
Line 41, in claim No. 24, delete referenced claim No. "1" and insert -- 23 --, therefor.

Signed and Sealed this

Sixteenth Day of July, 2002

Attest:

JAMES E. ROGAN
Attesting Officer          Director of the United States Patent and Trademark Office